US012782263B2

(12) United States Patent
Kolari et al.

(10) Patent No.: US 12,782,263 B2
(45) Date of Patent: Nov. 3, 2026

(54) METHOD FOR ESTIMATING THE VAPOR PHASE CORROSION LOAD

(71) Applicant: KEMIRA OYJ, Helsinki (FI)

(72) Inventors: Marko Kolari, Helsinki (FI); Iiris Joensuu, Helsinki (FI)

(73) Assignee: KEMIRA OYJ, Helsinki (FI)

(*) Notice: Subject to any disclaimer, the term of this patent is extended or adjusted under 35 U.S.C. 154(b) by 155 days.

(21) Appl. No.: 18/781,230

(22) Filed: Jul. 23, 2024

(65) Prior Publication Data

US 2024/0377312 A1 Nov. 14, 2024

Related U.S. Application Data

(62) Division of application No. 17/297,309, filed as application No. PCT/FI2019/050842 on Nov. 27, 2019, now Pat. No. 12,072,279.

(51) Int. Cl.
*G01N 17/04* (2006.01)
*G01N 33/34* (2006.01)

(52) U.S. Cl.
CPC ........... *G01N 17/04* (2013.01); *G01N 33/343* (2013.01)

(58) Field of Classification Search
CPC ....... G01N 17/04; G01N 33/343; G01N 25/56
USPC .......................................................... 324/700
See application file for complete search history.

(56) References Cited

U.S. PATENT DOCUMENTS

| | | | | |
|---|---|---|---|---|
| 9,016,110 B2* | 4/2015 | Seifert | G01N 33/18 | 73/61.43 |
| 11,054,362 B2* | 7/2021 | Howland | C12Q 1/04 | |
| 2003/0020029 A1* | 1/2003 | Henry | G01N 21/64 | 250/559.4 |
| 2010/0147056 A1* | 6/2010 | Stolle | G01N 25/56 | 73/86 |
| 2013/0192337 A1* | 8/2013 | Ashton | G01N 33/18 | 73/19.1 |
| 2014/0343872 A1* | 11/2014 | Ilmola | G01N 33/1826 | 702/25 |
| 2015/0000853 A1* | 1/2015 | Kolari | D21H 21/36 | 162/252 |
| 2015/0119286 A1* | 4/2015 | Whitfield | G01N 17/002 | 422/53 |

* cited by examiner

*Primary Examiner* — Christopher P Mcandrew
(74) *Attorney, Agent, or Firm* — Meunier Carlin & Curfman LLC

(57) ABSTRACT

The present invention relates to a method for estimating vapor phase corrosion load in a paper or board manufacturing system, method for controlling vapor phase corrosion load in a paper or board manufacturing system and an arrangement usable is those method. Said methods allow easy on-line follow up of the corrosion load and also adjusting biocide dosage.

4 Claims, 7 Drawing Sheets

METHOD FOR ESTIMATING THE VAPOR PHASE CORROSION LOAD

PRIORITY

This application is a divisional of U.S. application Ser. No. 17/297,309, filed May 26, 2021, which is a U.S. national stage application of the international application number PCT/FI2019/050842 filed on Nov. 27, 2019, and claiming priority of FI20186005 filed on Nov. 27, 2018, the contents of which are incorporated herein by reference.

FIELD OF INVENTION

The present invention relates to a method for estimating vapor phase corrosion load in a paper or board manufacturing system, method for controlling vapor phase corrosion load in a paper or board manufacturing system and an arrangement usable in those method.

BACKGROUND

A common problem in paper and pulp processing systems is biofilm, or slime, formation caused by bacterial growth in the various process waters and resulting in slime formation on surfaces in the system. It is desirable to both minimize bacteria in the process waters and to prevent biofilm formation on the system surfaces. A traditional method for controlling biofilm problems is to add microbe control chemicals to the process waters. Oxidising biocides is one commonly used class of control chemicals.

Halogenated hydantoins are known oxidizing biocides and effective at killing microbes in pulp and paper systems without adverse effects on the chemical additives used in the system and without remarkable corrosion load.

Haloamines, such as chloramines and bromamines, are also known oxidizing biocides. Haloamines can be formed by combining an ammonium source, such as ammonium sulphate, ammonium chloride, ammonium bromide, ammonium phosphate, ammonium carbonate, ammonium carbamate, ammonium nitrate or any other ammonium salt, including urea, with an oxidant such as sodium hypochlorite. Haloamines are becoming a more preferred chemical for microbe control of paper and pulp processing systems. Haloamines are effective at minimizing bacteria levels in the process waters and preventing slime formation on system surfaces, but as easily volatile they can reach machine structures above water level being susceptible to corrosion.

Corrosion is a concern in the “short loop,” or short circulation section, of a paper machine, and in the subsequent press and drying section. In a typical pulp paper or board manufacturing process, pulp stock is passed into a headbox, which distributes the pulp stock onto a moving wire in a forming section. The paper sheet is formed in the forming section and then sent to presses and dryers for finishing. The short loop is a system that recirculates and recycles excess water from the pulp stock. The excess water is collected in a wire pit in the forming section and then a major portion thereof is recirculated back to the headbox for reuse. Although many tanks, lines and other immersed structures of pulp and paper systems are typically formed from acid-proof stainless steel, many components above the water surface level, and components in the press and dryer section, are formed from milder steel materials. Especially these components are thus adversely affected by gas phase corrosion when volatile oxidizers, such as haloamine or chlorine dioxide chemistries are utilized for microbe control.

WO 2013/107941 A1 discloses a method for monitoring the corrosion caused by biocide in a machine. The information on corrosion is obtained using a sensitised electrical resistance probe located inside the machinery.

There is a constant need for means of controlling the microbial purity without causing unnecessary corrosion load due to overdosing of oxidative biocides. The cost savings resulting from using effective oxidative biocide control should not be compromised by additional repair costs due to the vapor-phase corrosion in the systems. It would be desirable to employ a chemical method for microbe control that benefits from the cost savings achievable using oxidative biocides and that simultaneously minimizes gas-phase corrosion of structural and functional metal components of the machinery. Especially there is a need to have easier means to follow the risk on-line.

SUMMARY

The present disclosure generally relates to an optimisation of oxidative biocide content in aqueous solutions, suspension and/or slurries in a paper or board manufacturing system. More specifically the disclosure addresses an estimation and controlling the corrosion load caused by stabilized halogen compounds such as haloamines.

The first aspect of the invention is a method for estimating vapor phase corrosion load in a paper or board manufacturing system.

The second aspect of the invention is a method for controlling vapor phase corrosion load in a paper or board manufacturing system.

The third aspect of the invention is an arrangement for use in connection with paper or paper manufacturing system.

Characteristics features of the above aspects are depicted in the independent claims.

DETAILED DESCRIPTION

Figure 1:
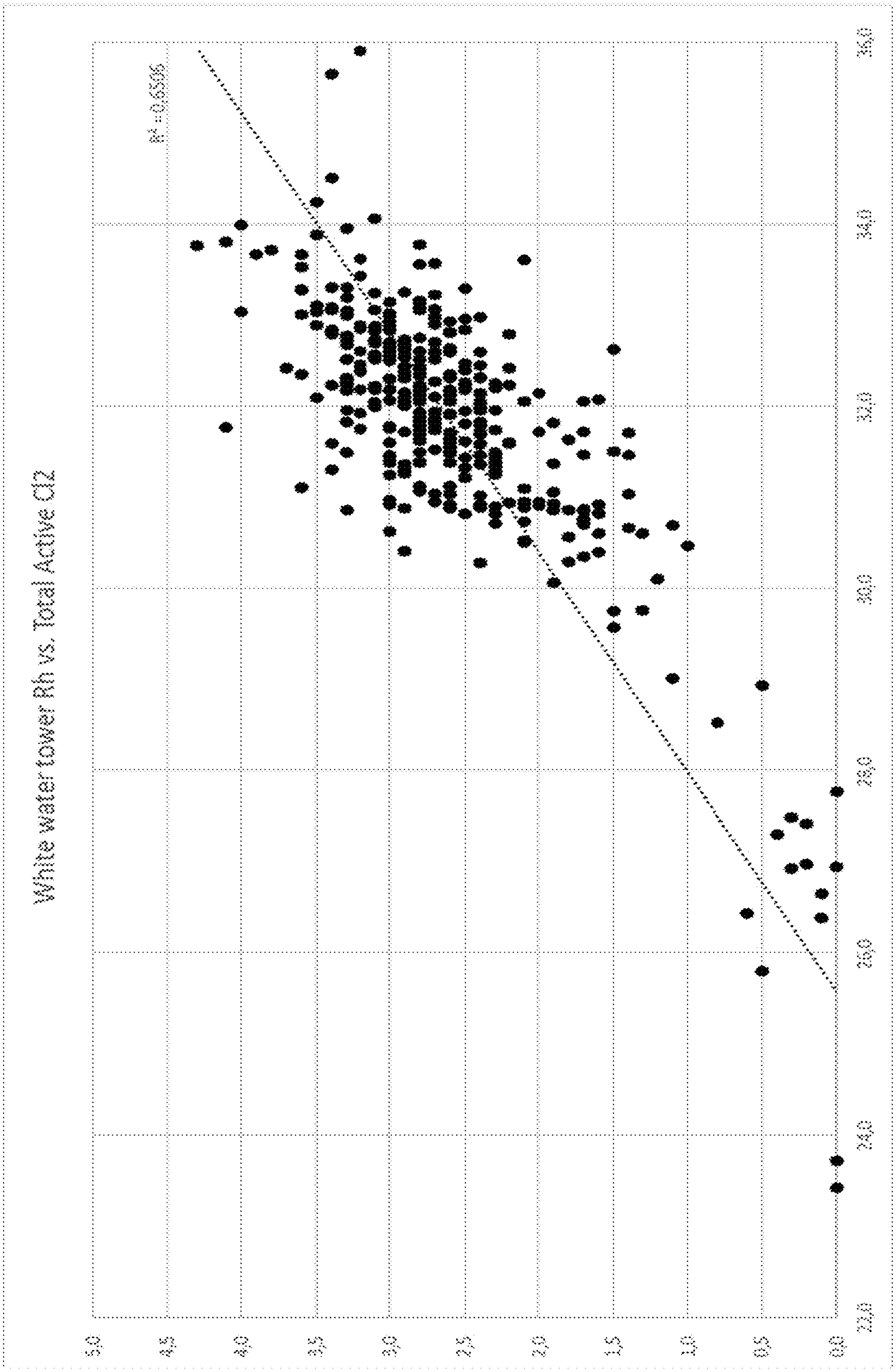
FIG. 1 shows a correlation between rH values and total active chlorine residuals in circulating water storage tower of a fine paper machine.

Current practices have shown that keeping the paper or board manufacturing system free of harmful microbial activity and biofilm formation with continuous or periodical addition of haloamine or chlorine dioxide in the system is needed. Excess dosage of biocide may cause a risk for gas phase corrosion. The inventors have shown that an effective microbial control using oxidative biocides results in a certain minimum amount of active halogen(s), such as active chlorine, in a vapor phase. It is known that high amounts of halogens in vapor phase of paper or board manufacturing system increase the corrosion load caused by oxidative biocides and risk on corrosion. The inventors have surprisingly shown that there is a correlation between rH values exceeding a determined rH threshold value of an aqueous suspension, slurry or solution in a paper or board manufacturing system and the corrosion load in said paper or board manufacturing system. Active chlorine (total active chlorine residuals) or halogens in vapor phase cause corrosion in a course of time.

The present invention relates to a method for estimating vapor phase corrosion load in a paper or board manufacturing system. The method comprises the steps of:

i. determining in a defined location of an aqueous process flow a threshold rH value being characteristic for said flow and said location; and
ii. determining rH values of said aqueous flow in said defined location over a defined time period in defined (multiple) time points; and
iii. calculating ΔrH in each time point as a difference between a determined rH value (a respective of one of the determined values) and the predetermined rH threshold value obtained in step (i), wherein the calculated value ΔrH is at least zero (zero or more); and
iv. calculating ΣΔrH as a cumulative sum of ΔrH values obtained in step (iii).

Alternatively, steps (iii) and (iv) above are replaced by v. calculating cumulative sum of each determined rH value obtained in step (ii) wherein the determined rH value is at least the predetermined rH threshold value obtained in step (i); and
vi. calculating ΣΔrH as a difference between the cumulative sum obtained in step v and the threshold value obtained in step (i) multiplied with the defined number of time points (on other words calculating a cumulative threshold rH).

The ΣΔrH obtained in step (iv) or (vi) is used to estimate the corrosion load by comparing to earlier ΣΔrH value from the same location, wherein increase in ΣΔrH indicates an increase in corrosion load and decrease in ΣΔrH indicates a decrease in corrosion load. In one embodiment the corrosion load is estimated in relation to the corrosion load determined earlier in a similar manner in said location.

In this connection expression "the corrosion load determined earlier in a similar manner in said location" means that the location of the aqueous process flow, the time period for determinations and the number of time points are similar. Said location may be any location where aqueous process flow (such as process water, broke, pulp slurry) with biocide is present. In one embodiment the location of the determination is circulating water, in short or long water circuits, or clear filtrate, cloudy filtrate, super clear filtrate, or shower water.

In one embodiment the ΣΔrH obtained in step (iv) or (vi) is used to estimate the corrosion load in relation to the corrosion load at the determined threshold rH or to the corrosion load defined earlier for said (respective) aqueous flow in said defined location over a defined time period in defined (multiple) time points, wherein increase of 2 ΔrH indicates an increase in corrosion load and decrease in ΣΔrH indicates a decrease in corrosion load. 2 threshold rH is a cumulative sum of rH values determined in optimal conditions. Thus, a positive ΣΔrH in relation to Σthreshold rH is an indication that there may be unnecessary corrosion load due to excess dosage of oxidizing biocides.

The method allows estimating and following the corrosion load on-line throughout the production period in between the shut downs of the paper and board manufacturing process or during selected periods. Up-to-date information on corrosion load using on-line measurements and mathematical models allows enhanced control of overall biocide status and thereby avoiding unnecessary corrosion load without compromising the microbial control.

It is clear to a person skilled in the art that respective cumulative sum (ΣΔrH) can be obtained using various calculation systems by following the principle of summing together rH values higher than the predetermined threshold value so that values lower than said threshold are calculated as said threshold value, or as zero, if ΔrH values are used. In other words, ΔrH has never negative value, possible negative value is replaced by zero when calculating a cumulative sum.

In this connection defined location simply means that the same determination location (or site) is used for each determination. In a paper or board manufacturing system the conditions are not constant but vary in different locations.

In this connection a defined time period means the period of time during which the determinations are made.

In this connection defined time points mean that the number of determinations are in line with the number of threshold values. Typically, multiple time points (several measurement events) are used. In addition, term defined time points may mean that the determination events take place in defined (known) interval.

Constant measurement parameters (location, time point, time period) allow comparing separate determinations of cumulative ΔrH (e.g. weekly or monthly determinations) to obtain information of possible changes in corrosion load.

The rH values lower than the predetermined threshold value indicate that the biocide content may not be efficient for bacterial control. At rH values lower than said threshold the halogen residuals are consumed rapidly and therefore the amount of active halogen in vapor phase and corrosion load are not significantly affected. Essential in the method is that the number of determination points and the time period corresponds the number of predetermined ΔrH values. As the corrosion load is to be estimated, it is also essential that ΔrH value for a determination point used in calculation should never be negative; i.e. values lower than the predetermined threshold values are 'neutralized'.

Methods for estimating effectiveness of microbial control are known within the art and e.g. U.S. Pat. No. 7,837,883. Suitable biocide dosage level provides significant antimicrobial effect, with reduced or eliminated microbiological disturbances to production of paper and board. In this connection efficient bacterial control means a state where no biofilm formation or for example bad odour issue exists. A bacterial control may also be deemed efficient when the count of aerobic bacteria calculated as colony forming units per millilitre in aqueous system of a paper or board manufacturing system is reduced by 3 log 10 when compared to a system without any bacterial control.

In paper or board manufacturing system a minimum 3 log 10 reduction in amounts of viable microorganisms over a 24 hours period (cultivation result) may be deemed an effective microbial control. Alternatively, a 90% reduction in activity of microorganism in process circuits over a 24 hours period (ATP-results) may be deemed an effective microbial control. The method disclosed here is suitable for estimating corrosion load caused by oxidative biocides, specifically stabilized halogen compounds, such as haloamine biocides.

In an embodiment the biocide is haloamine. The haloamine may be a monohaloamine, dihaloamine, trihaloamine, or a combination thereof. Monohaloamines are preferred. Volatility of monochloramines is lower than volatility of di- and trichloroamines and thus it is safer to use.

In an embodiment the biocide is monochloramine, monobromamine, bromochloroamine or a combination thereof, formed by combining an ammonium source and an oxidant in the presence of dilution water.

In an embodiment the biocide is chloramine, especially monochloramine. Monochloramine is an efficient biocide and has a known safety profile.

The redox value (rH) is dependent on pH and temperature. Determination of rH value thus involves measurement of temperature, pH and redox potential. The rH value may be determined (calculated) using the pH and redox potential using equation (1):

$$rH = 2*\mathrm{pH} + 2*Eh*F/(c*R*T) \quad (1)$$

wherein F=Faraday constant ($9.64853399\times10^{4}$ C $mol^{-1}$, c=ln 10, T=temperature (K), Eh=redox potential measured with standard hydrogen electrode, and R=universal gas constant (8.314472 J $K^{-1}$ $mol^{-1}$). In one embodiment of the invention rH is determined using equation (1).

Temperature, pH and redox measurements are known, sometimes routine measurements of aqueous process flow as such are used in monitoring the process state. Thus, performing a method according to the invention does not necessarily require any additional or separate measurement equipment.

In an embodiment the (pre) defined time period for determining a cumulative ΔrH (ΣΔrH) value is at least 12 hours, at least 24 hours, at least 48 hours, at least 7 days, at least 30 days. In well-functioning microbe control system the biocide dosage is optimized the vapor corrosion rate is slow. Thus, it may be appropriate to use time periods of weeks or months. However, in connection of microbial problems requiring for example periodical strong dosing of the oxidative biocides or during optimization efforts for balancing the dosage it may we useful to use shorter periods of time. In one embodiment the cumulative ΔrH (ΣΔrH) is followed by repeating the determination in the same location using the same parameters after a time period, e.g. using a determination time of few hours in every second day and comparing them to follow the possible change in corrosion load. In one embodiment the determination is repeated once a week for one day period. In one particular embodiment the ΣΔrH is measured in respective time periods of a paper or board manufacturing run cycle (meaning a production period between the shut downs) in order to obtain information of changes in the manufacturing process.

In one embodiment the cumulative sum for a predefined period of time is calculated as a moving sum, where the number of determination time points remains constant when the last determined value is added to the sum and the oldest is excluded from the calculation.

In one embodiment the cumulative sum for a longer period (e.g. a week, a month, quarter or full year) can be based on hourly, daily or weekly average of ΔrH's.

In an embodiment at least one time point per 24 hours is determined or wherein at least one time point per 1 hour is determined wherein at least one time point per 10 minutes is determined, wherein at least one time point per 1 minute is determined or wherein at least one time point per 1 second is determined. A person skilled in the art is able to select suitable frequency of measurement using his knowledge on the water circulation in the system, location where biocide is added, and characteristics of the aqueous mass and biocide used. Especially in connection of pulse dosage of biocides it may be beneficial to use high frequency for determinations.

Typically, when the process requires changes to biocide dosage it may be beneficial to have determinations with a short time interval.

Typical reasons for loss of control include feed equipment failure or under-dosing to reduce cost. Thus, effective biocide control is needed. An over-dosing of biocide causes increased chemical costs. Other problem is a corrosion load caused by excess active halogens.

Total active halogens may be measured using methods known within the art such as DPD method announcing the amount as total active chlorine. The method is appropriate for waters, where active halogens like chlorine, bromine or iodine are present. It is based on formation of red DPD colour complex and measurement of the absorption in a photometer or quantifying the colour intensity by visual comparison of the colour with a scale of standards.

In one embodiment the total active halogen is measured using ISO 7393-2:2017 standard. Total active chlorine may be determined using HACH DPD Method 10250 (Hach Company/Hach Lange GmbH). Total active bromine may be determined using HACH DPD Method 8016 (Hach Company/Hach Lange GmbH). In an embodiment the predetermined threshold rH value is selected as an rH-value determined at lowest effective oxidative biocide content for said system. In an embodiment the lowest effective oxidative biocide content results in 1 ppm of total active chlorine residual in an aqueous solution or slurry. Thus, in one embodiment the optimal rH value for a defined location corresponds to rH value measured when there is 1 ppm of total active chlorine residual in an aqueous solution or slurry. Alternatively, the optimal rH value, used as a threshold value in the methods here described, is slightly above the threshold value. For example, when the threshold value is determined to be rH 28, the target rH may be within range rH 28 to 28.2.

In an embodiment rH values are determined using on-line system, said system including means for pH, redox and temperature measurements. In addition, the system may comprise means for determining the rH value. On-line measurement allows a person skilled in the art an easy determination with short time interval. The automated processing of data allows following the biocide dosage on minute, hourly, daily, weekly, monthly or yearly basis. In addition. it allows easy comparison of data between defined production periods of paper or board manufacturing process.

Typical run cycle for paper or board manufacturing is 6 to 8 weeks after which there is a machine shut down for e.g. system boil out (maintenance break). In one embodiment the changes in corrosive load and also need for microbial control between the run cycles are followed by comparing ΣΔrH values between run cycles at the same manufacturing system.

The present invention relates also to a method for controlling a vapor phase corrosion load in a paper or board manufacturing system. Said method comprises the steps of:

i. determining in a defined location of an aqueous process flow a threshold rH value characteristic to said flow and location; and
ii. determining rH values of said aqueous flow in said defined location over a defined time period in defined multiple time points; and
iii. calculating ΔrH in each time point as a difference between a determined value (a respective of one of the determined rH value) and the predetermined rH threshold value obtained in step i, wherein the calculated value ΔrH is at least zero (i.e. zero or more, i.e. ΔrH has never a negative value, possible negative value is replaced by zero); and
iv. calculating ΣΔrH as a cumulative sum of ΔrH values obtained in step iii or alternatively v. calculating cumulative sum of each determined rH value obtained in step ii wherein the determined rH value is at least the predetermined rH threshold value; and vi. calculating ΣΔrH as a difference between the cumulative sum obtained in step v and the threshold value obtained in step i multiplied with the defined number of time points;

wherein a cumulative ΔrH value for the predetermined time period is used to estimate the corrosion load; and vii. using the estimate to determine how to adjust the dosing of an oxidizing biocide in a paper or board making process; and viii. adjusting the amount of the oxidizing biocide based on the estimate obtained regarding vapor phase corrosion.

In addition to adapting the dosage of the biocide it is also possible to select suitable dosing point.

In an embodiment the method further comprises observing determined values lower that said threshold value before step (v). These values show that the amount of biocide may not be efficient for proper bacterial control.

The present invention relates an arrangement for use in connection with paper or paper manufacturing system, comprising:

i. at least one computing device; and ii. a method application executable in the at least one computing device, the method application comprising:

logic that obtains information regarding the estimated load of vapor phase corrosion over a time period; and logic that uses the information to determine how to adjust the dosing of an oxidizing biocide in a paper or board making process.

In one embodiment the logic that obtains information regarding the estimated load of vapor phase corrosion over a time period comprises calculating ΣΔrH.

In one embodiment the logic that obtains information regarding the estimated load of vapor phase corrosion over a time period comprises the steps of the method for estimating vapor phase corrosion load in a paper or board manufacturing system as disclosed here.

In an embodiment the arrangement comprises also means for alerting when determined rH value or cumulative sum of determined rH values are higher than the threshold value.

In an embodiment the arrangement comprises means for alerting values lower than the predefined threshold value.

In an embodiment the arrangement comprises automated means for dosing the oxidizing biocide.

Automated system allows gathering and processing extensive amount of data and using it for controlling biocide dosage to optimize the bacterial control, corrosion risk and costs of the process.

The features and benefits discussed in connection of a method for estimating vapor phase corrosion load in paper of board manufacturing system are applicable also to a method for controlling vapor phase corrosion load in paper of board manufacturing system and an arrangement here disclosed and vice versa.

The invention is illustrated below by the following non-limiting examples. It should be understood that the embodiments given in the description above and the examples are for illustrative purposes only, and that various changes and modifications are possible within the scope of the invention.

EXAMPLES

Example 1: Correlation Between rH and Total Active Chlorine Residual in Paper Machine White Water System Using MCA as a Biocide for Controlling Microbial Growth Treatment of paper machines with MCA is a common biocide approach. Bacterial counts (cfu/ml), rH values and amount of total active chlorine were analysed from an aqueous sample taken from circulating water storage tower of a fine paper machine.

Total active chlorine (Cl2) was measured manually using Total Chlorine DPD Method for Powder Pillows by HACH according to instructions by manufacturer (Method 10250; Hach Company/Hach Lange GmbH).

rH was determined using equation (1).

$$rH = 2*\mathrm{pH} + 2*Eh*F/(c*R*T) \tag{1}$$

Amounts of aerobic bacteria were quantified by plate count method commonly used within the field.

Measurement of bacterial amounts in white water showed that in this process the presence of minimum 1 ppm of total active chlorine residual was required for reduction of bacterial amounts by 3 logarithmic units, which was considered to provide effective microbe control. FIG. 1 shows how the measured total active chlorine values correlated with the rH values. It is shown that when following oxidative status of the system (on-line measurement of rH value) no good microbe control can exist if rH value is below 28. Thus, for this aqueous flow and location a threshold value to be used in calculating ΔrH values is 28.

The data obtained shows that for this machine and this location you need to have above rH 28 all the time in order to maintain effective microbial control.

Example 2: Delta rH

Figure 2A:
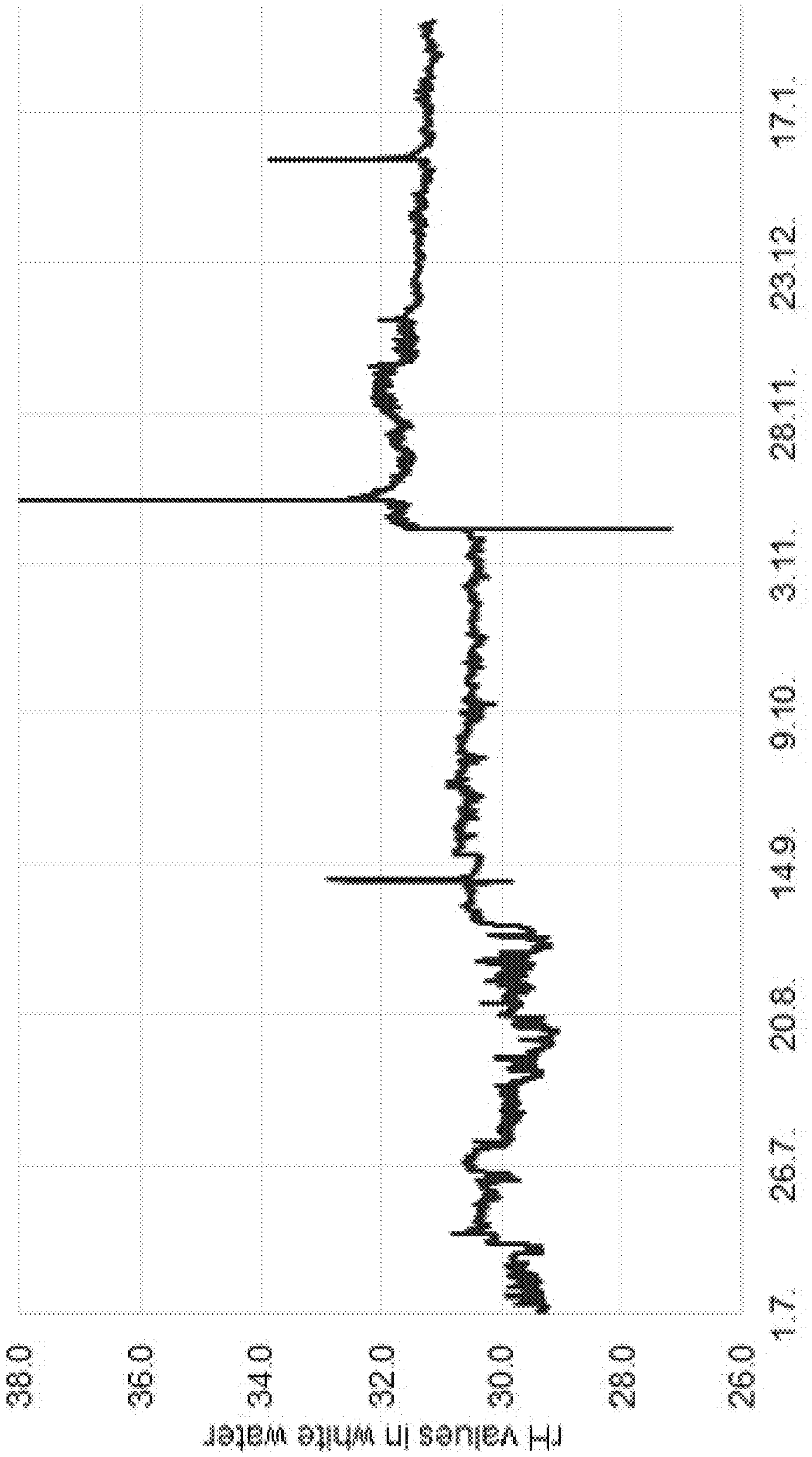
FIG. 2 shows rH values (2*a*) and A rH values (2*b*) measured 24 times per day from one location in recirculating process water system of a paper machine.
Figure 2B:
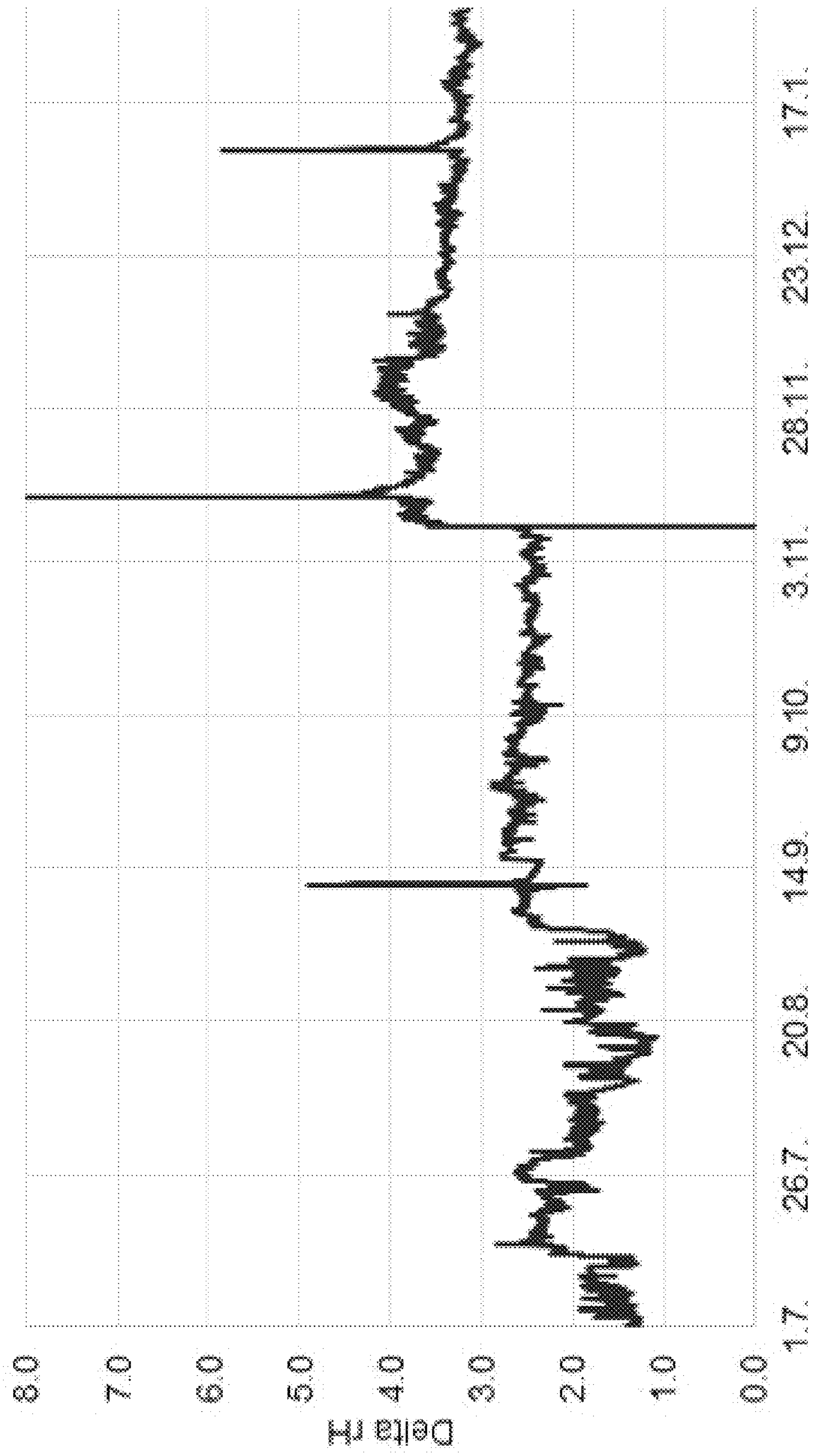

FIGS. 2*a* and 2*b* show rH and ΔrH values measured from one location in recirculating process water system of a paper machine. Graph is based on 24 daily determinations. FIG. 2*a* shows the determined rH values and 2*b* shows respective ΔrH values i.e. difference between the determined rH value and the threshold (determined as explained in Example 1 above). During this determination period rH has been high and the delta values are positive. A higher positive ΔrH value indicates presence of higher amounts of excess monochloramine and increased corrosion load.

Example 3: Cumulative ΔrH

Figure 3A:
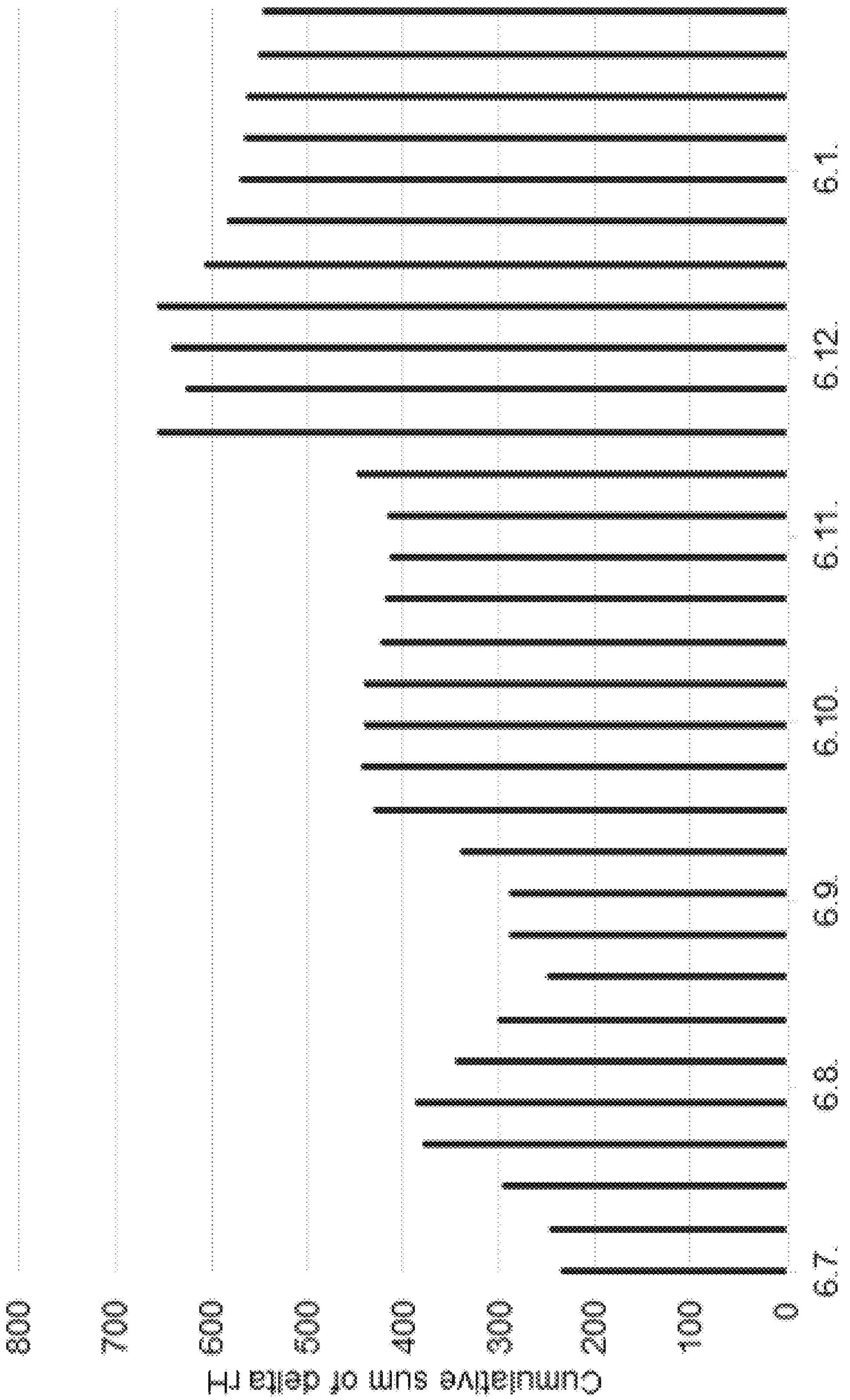
FIG. 3 shows a weekly cumulative sum (3*a*) and a moving cumulative sum (3*b*) of the same A rH determinations.
Figure 3B:
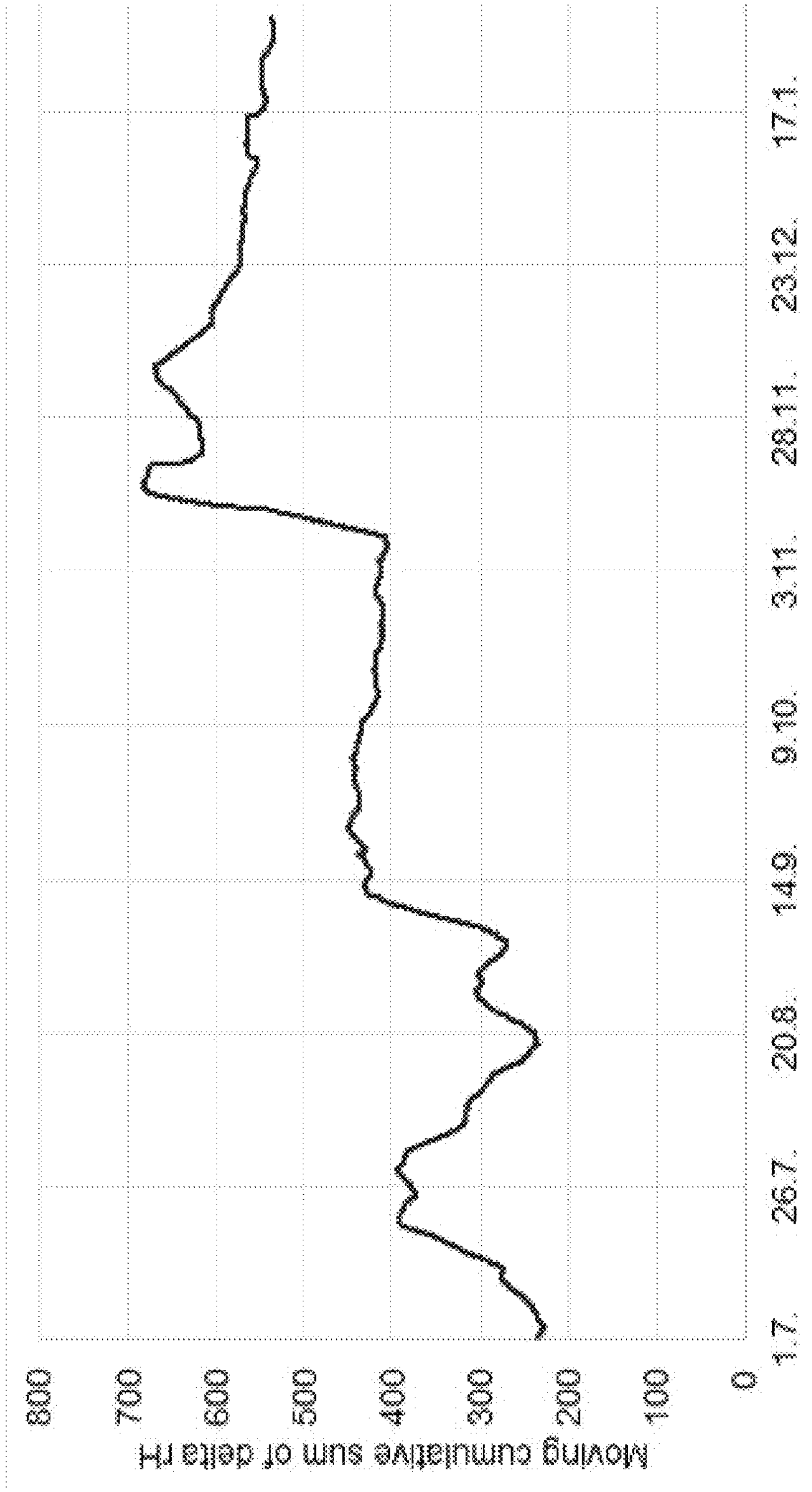

The rH was determined and ΔrH calculated as explained in examples 1 and 2. FIG. 3*a* shows a weekly cumulative sum and FIG. 3*b* shows a moving cumulative sum. The determinations of rH have been made one per hour and time period used for calculating cumulative sum has been once week (i.e. 168 measurement time points or determination events). Weekly cumulative sums for first four months (time period from 1.7. to 8.11. i.e. 1 July to 8 November) were lower comparing to weekly cumulative sums for time period between 8.11.-1.2. i.e. 8 November to 1 February). This indicates higher corrosion load in time period between 8.11.-1.2. (8 November to 1 February).

Figure 4A:
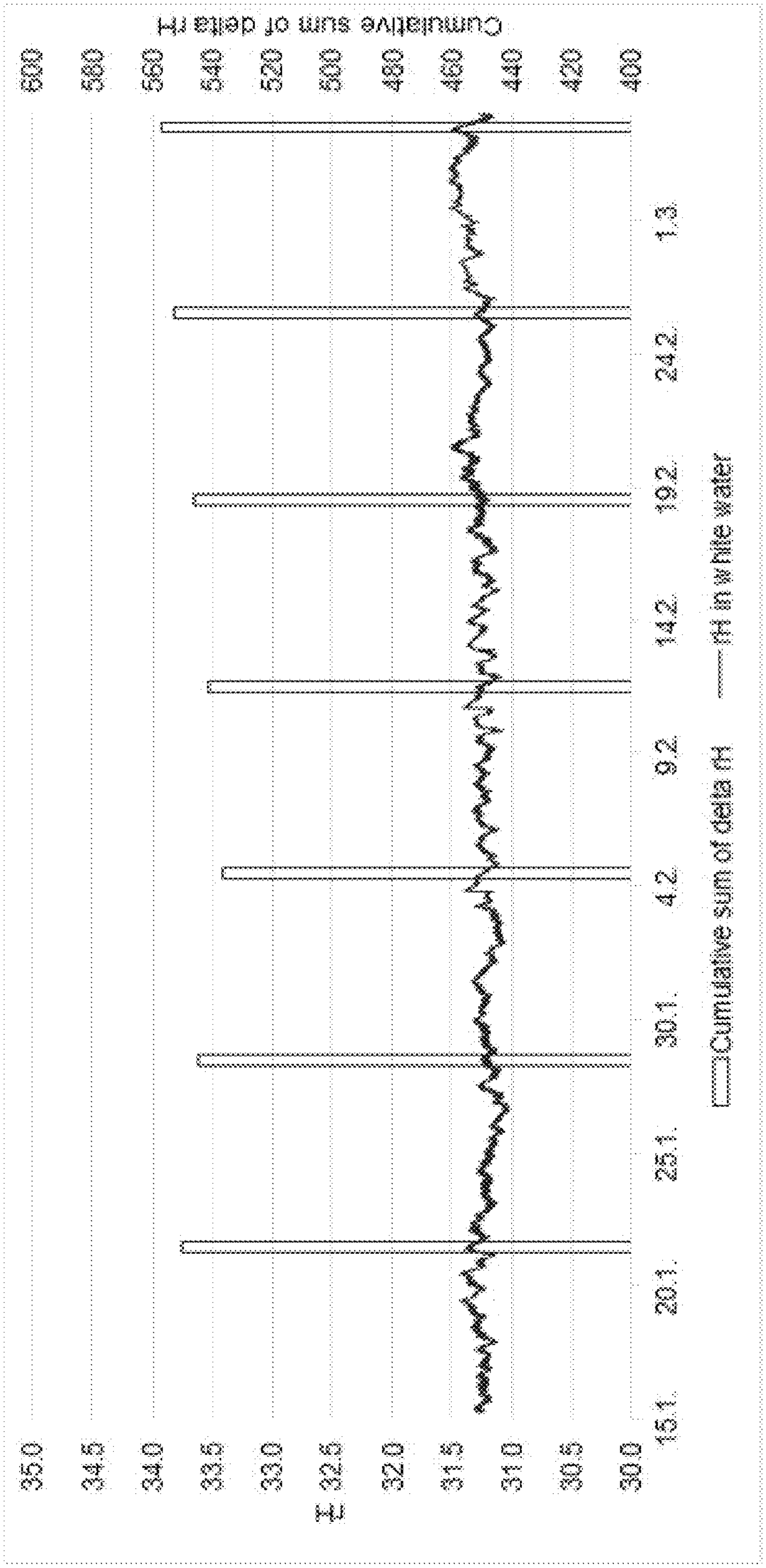
FIGS. 4*a* and 4*b* show a comparison data of one week a cumulative Δ rH values between two time periods with different biocide dosing patterns.
Figure 4B:
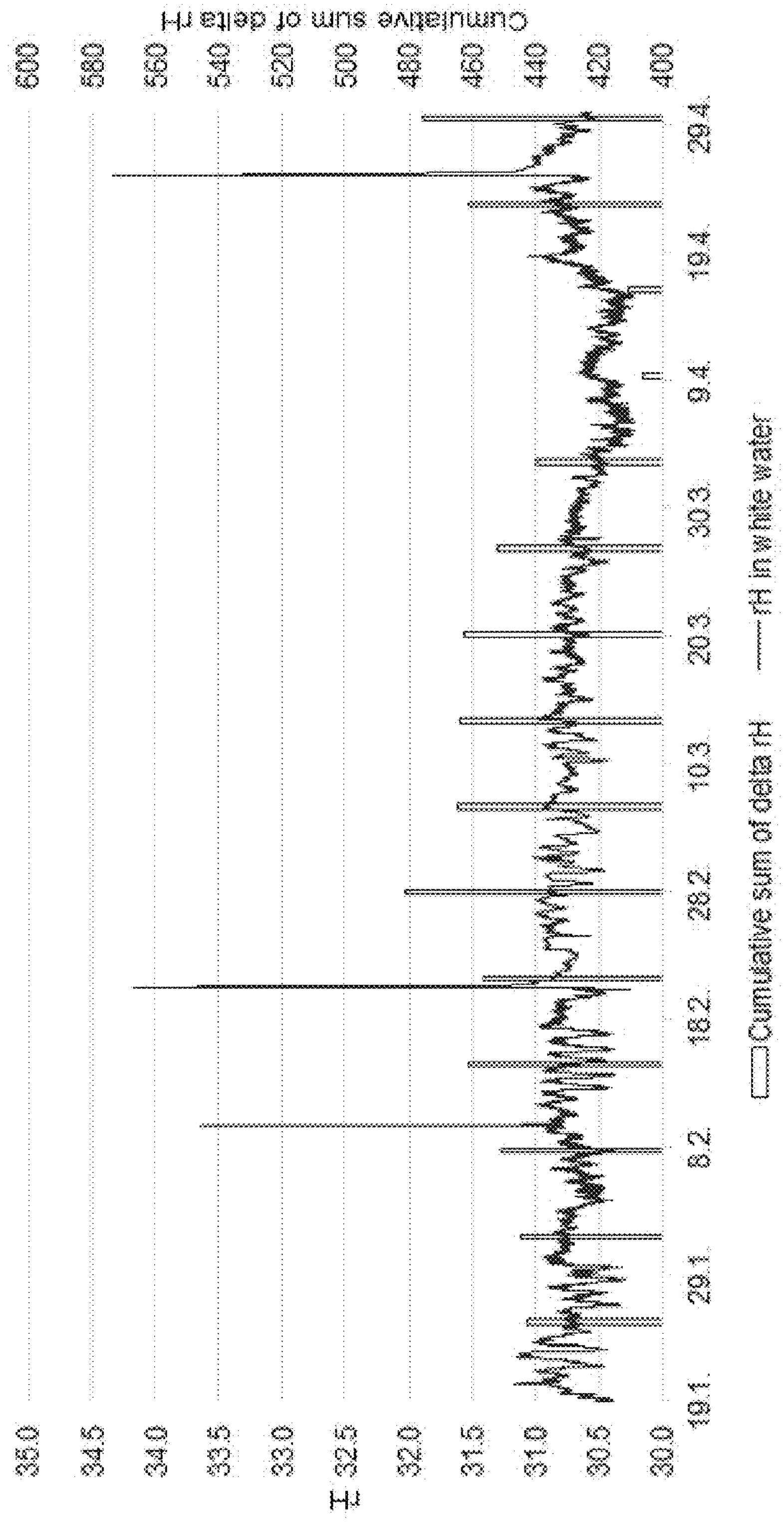

Example 4: Comparison of Corrosion Load Caused by Different Biocide Dosing Patterns ΔrH values were measured and calculated as explained in examples 1 and 2. Threshold value was Rh 28. FIG. 4*a* shows a situation where rH was relatively stable but was constantly also exceeding the threshold value clearly. The determined cumulative ΔrH sum was >500 in all time periods. The determinations were repeated in a situation where rH was typically in a slightly lower level (still exceeding the threshold value 28), but due to periodical stronger pulse dosages of biocides some high peak Rh values were also observed (FIG. 4*b*). The cumulative sum, however, was <500 showing that the overall corrosion load from this dosing pattern was lower, despite of the occasional pulse dosages.

The invention claimed is:

1. A system for monitoring vapor phase corrosion load in a paper or board manufacturing system comprising:

i. at least one computing device comprising logic that executes an application to perform a method, the method comprising:

obtaining measurements from the paper or board manufacturing system regarding the estimated load of vapor phase corrosion over a time period, wherein the logic that obtains measurements regarding the estimated load of vapor phase corrosion over a time period comprises calculating ΣΔrH;

determining an adjustment dosage of an oxidizing biocide by comparing the obtained measurements to a threshold rH value; and adjusting an amount of the oxidizing biocide provided to the paper or board manufacturing system based on the determined adjustment dosage.

2. The system of claim 1, wherein the computing device is configured to display an alert when determined rH value or cumulative sum of determined rH values are higher than the threshold value.

3. The system of claim 1, wherein the computing device is configured to display an alert for measurements lower than a predefined threshold value.

4. The system of claim 1 further comprising an automated means for dosing the oxidizing biocide.

* * * * *